United States Patent
Munro

(10) Patent No.: US 10,018,593 B2
(45) Date of Patent: Jul. 10, 2018

(54) DUEL MODE ION MOBILITY SPECTROMETER

(71) Applicant: Smiths Detection-Watford Limited, Hertfordshire (GB)

(72) Inventor: William Angus Munro, Hertfordshire (GB)

(73) Assignee: SMITHS DETECTION-WATFORD LIMITED, Hertfordshire (GB)

( * ) Notice: Subject to any disclaimer, the term of this patent is extended or adjusted under 35 U.S.C. 154(b) by 0 days.

(21) Appl. No.: 15/515,842

(22) PCT Filed: Sep. 29, 2015

(86) PCT No.: PCT/GB2015/052835
§ 371 (c)(1),
(2) Date: Mar. 30, 2017

(87) PCT Pub. No.: WO2016/051161
PCT Pub. Date: Apr. 7, 2016

(65) Prior Publication Data
US 2017/0248546 A1    Aug. 31, 2017

(30) Foreign Application Priority Data
Sep. 29, 2014    (GB) .................................. 1417185.4

(51) Int. Cl.
*H01J 49/00* (2006.01)
*G01N 27/62* (2006.01)
*H01J 49/06* (2006.01)

(52) U.S. Cl.
CPC ........ *G01N 27/622* (2013.01); *H01J 49/0027* (2013.01); *H01J 49/061* (2013.01)

(58) Field of Classification Search
CPC ... G01N 27/622; H01J 49/0027; H01J 49/061
USPC .................................... 250/281, 282, 288
See application file for complete search history.

(56) References Cited

U.S. PATENT DOCUMENTS

| 2004/0011952 A1 | 1/2004 | Johnston et al. |
| 2008/0078928 A1 | 4/2008 | Wang et al. |

OTHER PUBLICATIONS

International Search Report dated Feb. 2, 2016 for PCT/GB2015/052835.
Szumlas, Andrew W. et al., "Design and construction of a mechanically simple, interdigitated-wire ion gate", Review Scientific Instruments, AIP, Melville, NY, vol. 76, No. 8, Aug. 12, 2005, pp. 86108-1-86108-3.

*Primary Examiner* — Nicole Ippolito
*Assistant Examiner* — Hanway Chang
(74) *Attorney, Agent, or Firm* — Kevin E. West; Advent, LLP

(57) ABSTRACT

An ion mobility spectrometer (100) comprising a first ion source (102-1, 108-1) for providing positive ions to be analyzed, an electric field applier arranged to provide an electric field configured to move the positive ions in a first direction towards a first ion detector (106-1, 110-1) adapted for detecting the positive ions, and a second ion source (102-2, 108-2) for providing negative ions to be analyzed, wherein the electric field applier is arranged to move the negative ions in a direction opposite to the first direction, towards the first ion source (102-1, 108-1) and towards a second ion detector (106-1, 110-1) adapted for detecting the negative ions.

20 Claims, 2 Drawing Sheets

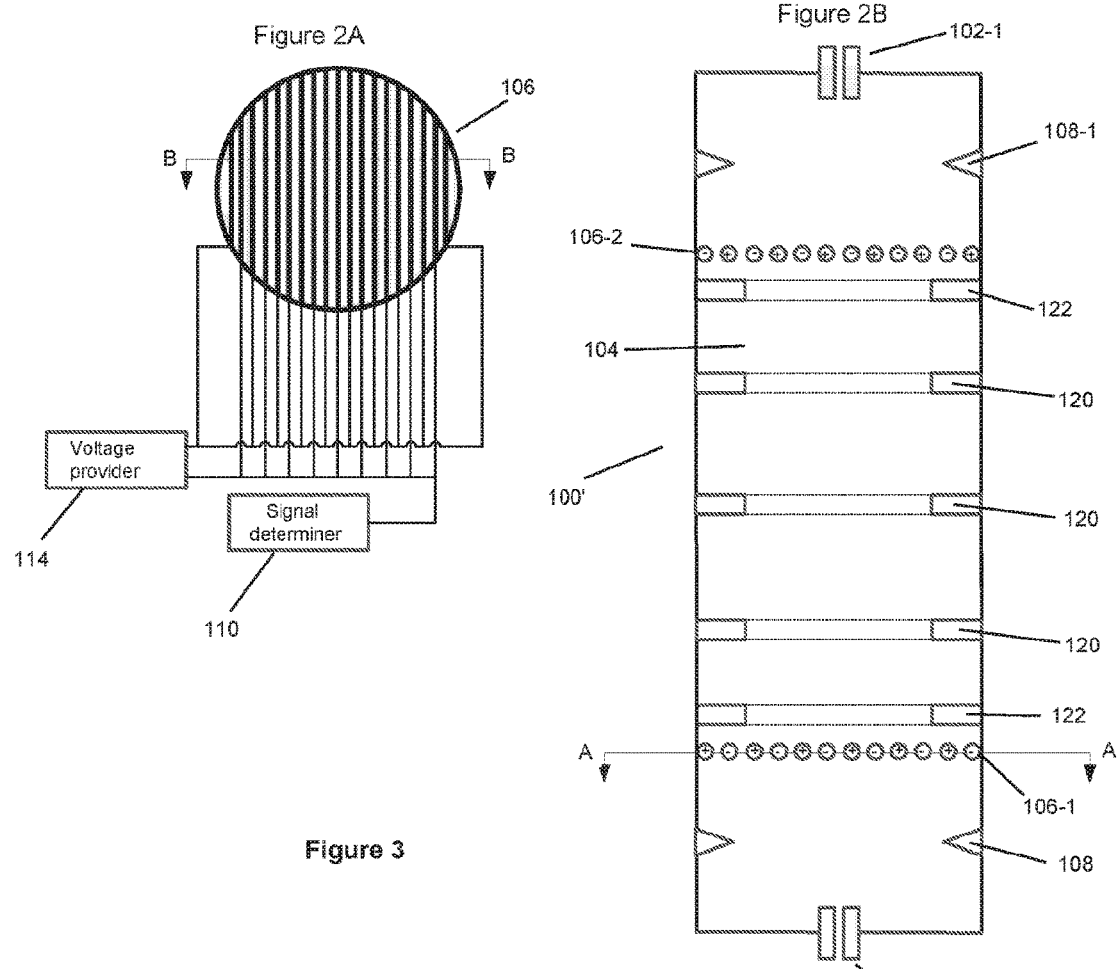
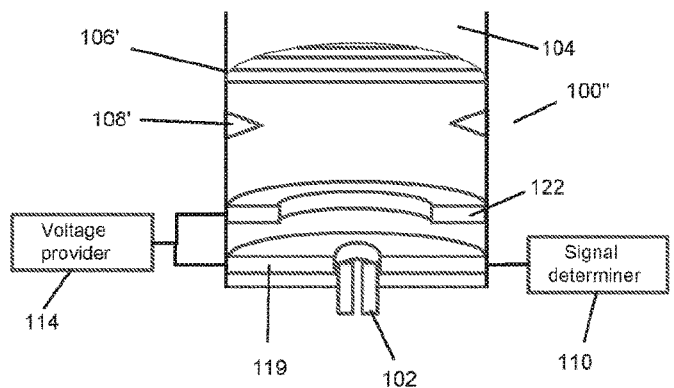

DUEL MODE ION MOBILITY SPECTROMETER

TECHNICAL FIELD

The present disclosure relates to ion mobility spectrometry methods and apparatus, and more particularly to methods and apparatus for time of flight ion mobility spectrometry, and still more particularly for methods and apparatus for use in dual-mode ion mobility spectrometry cells.

BACKGROUND

Ion mobility spectrometers (IMS) can identify material from a sample of interest by ionizing the material and measuring the time it takes the resulting ions to travel a known distance under a known electric field. Each ion's time of flight can be measured by a detector, and the time of flight is associated with the ion's mobility through a gas. An ion's mobility relates to its mass and collision cross section. Therefore, by measuring the time of flight of an ion in the detector it is possible to infer an identity for the ion. These times of flight may be displayed graphically or numerically as a plasmagram.

Different materials give rise to differently charged ions. Ion mobility spectrometry can be used for screening for traces of contraband such as explosives and narcotics. Narcotics may generally be detectable in an IMS operating in a positive mode, whereas narcotics may be detectable in negative mode. Some chemical weapons agents may be detected in positive mode, and others in negative modes. Some IMS devices therefore include both positive and negative mode cells.

Where space and electrical power resources are not limited the provision of both positive and negative mode IMS cells is unproblematic. In hand-held devices there are constraints on both size and weight of the device. The problem of dielectric breakdown of materials used in IMS power supply units also imposes a voltage related size constraint on IMS apparatus.

SUMMARY OF INVENTION

Aspects and examples of the invention are set out in the appended claims.

BRIEF DESCRIPTION OF DRAWINGS

Some embodiments will now be described, by way of example only, with reference to the accompanying drawings in which:

FIG. 2 is an illustration of a combined ion gate and detector for use in an IMS cell such as that illustrated in FIG. 1; and FIG. 3 is an illustration of a combined repeller electrode and detector for use in an IMS cell such as that illustrated in FIG. 1.

SPECIFIC DESCRIPTION

Figure 1:
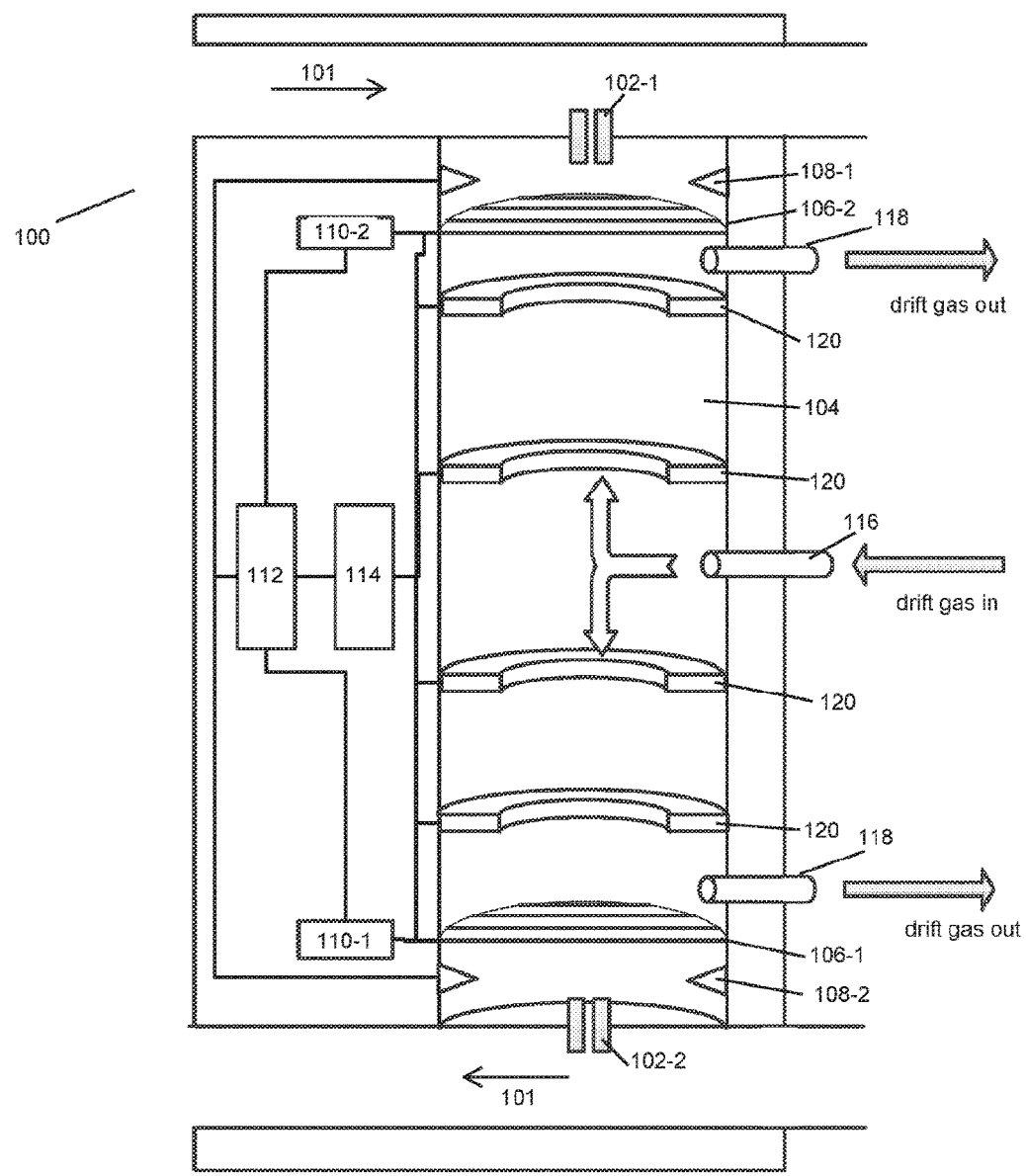
FIG. 1 shows a schematic cut-away view of an IMS cell.

An embodiment of the disclosure provides a dual mode IMS apparatus in which an electric field is provided to move positive ions along a drift chamber towards a detector of positive ions. The same electric field also moves negative ions in the other direction along the drift chamber towards a detector of negative ions. The detector of negative ions and the positive ion source on the one hand are separated by the drift chamber from detector of positive ions and the negative ion source on the other hand. Embodiments of the disclosure therefore provide a single dual mode IMS cell which may use a single voltage profile to move ions of different polarities in different directions. Embodiments of the disclosure may therefore use a single common power supply to move both the positive and negative ions. One example of such an IMS apparatus is illustrated in FIG. 1.

An embodiment of the disclosure also provides an ion gate adapted for use as a detector. Such ion gates may be used in the apparatus described with reference to FIG. 1. Another embodiment of the disclosure provides a repeller electrode adapted for operation as a detector. Such repeller electrodes may also be used in apparatus such as that described with reference to FIG. 1.

FIG. 1 shows an ion mobility spectrometer 100 comprising a drift chamber 104, a first ion source 102-1, 108-1, a second ion source 102-2, 108-2 a first ion detector 106-1, 110-1 and a second ion detector 106-2, 110-2. The first ion source 102-1, 108-1 and the second detector 106-2, 110-2 are arranged at one end of the drift chamber 104 and the second ion source 102-2, 108-2 and the first detector 106-1, 110-1 are arranged at the other end of the drift chamber 104.

The first detector 106-1, 110-1 may comprise a first collecting electrode 106-1 for collecting positive ions and a first signal determiner 110-1 coupled to the first collecting electrode 106-1. Similarly the second detector 106-2, 110-2 may comprise a second collecting electrode 106-2 for collecting negative ions and a second signal determiner 110-2 coupled to the second collecting electrode 106-2.

The first signal determiner 110-1 and the second signal determiner 110-2 may be coupled to a controller 112. The controller 112 may also be coupled to the first ion source 102-1, 108-1 and the second ion source 102-2, 108-2 and to an electric field applier arranged to provide an electric field for moving positive ions from the first ion source 102-1, 108-1 towards the first ion detector, and for moving negative ions from the second ion source 102-2, 108-2 to the second detector.

The electric field applier may comprise a plurality of electrodes and a voltage provider 114. For example, a series of drift electrodes 120 may be arranged along the drift chamber 104. The voltage provider 114 may be coupled to the drift electrodes 120 and to the first and second collecting electrodes. The voltage provider 114 and the drift electrodes 120 in the drift chamber 104 together provide a selected voltage profile along the drift chamber 104 to move positive ions in one direction along the drift chamber 104, and negative ions in the other direction (for example to move them in opposite directions). Accordingly, the same electric field moves positive ions toward the first collecting electrode 106-1, and negative ions towards the second collecting electrode 106-2. In some possibilities the electric field applier is arranged to provide a voltage profile that is symmetric about a mid-point of the drift chamber 104, for example the voltage profile at the mid-point of the drift chamber 104 may be based on a reference voltage, for example it may be grounded (e.g. coupled to a mid-point of a potential divider between the minimum and maximum supply voltages which define the voltage profile along the drift chamber 104).

The first signal determiner and the first collecting electrode are configured to operate together as a detector in which the first signal determiner provides a detection signal, such as a current or a voltage, based on the arrival of ions at the first collecting electrode. The first signal determiner is configured to provide this detection signal to the controller, and may also be configured to isolate the controller 112 from the voltage of the first collecting electrode (which may be at a very different voltage from the controller 112 due to the voltages applied to move ions along the drift chamber 104). For example, the first signal determiner may comprise an isolating op-amp. The second detector may be the same, and likewise the second collecting electrode may also be at a very different voltage from the controller 112 and so the second signal determiner may also be configured to provide a detection signal to the controller 112 and also to isolate the controller 112 from the voltage of the second collecting electrode.

The first ion source 102-1, 108-1 and the second ion source 102-2, 108-2 may each comprise an inlet 102, such as a pinhole or membrane, for introducing a sample of material to be ionised. They may also comprise an ioniser for applying ionising energy for ionising the material. Examples of ionisers include corona discharge sources and other sources of ionising radiation. The ionisers may be configured to be controlled by the controller 112 to select the timing of operation of the ionisers. Each inlet 102 may be arranged to obtain a sample of a gaseous fluid, such as a gas or vapour, from a flow 101 of gaseous fluid. The IMS may be arranged to provide the same flow of gaseous fluid past the inlet's of both the first ion source 102-1, 108-1 and the second ion source 102-2, 108-2. The first ion source 102-1, 108-1 and the second ion source 102-2, 108-2 may also each comprise an ion gate, such as a Bradbury-Nielsen gate or a Tyndall-Powell gate.

The drift chamber 104 may comprise a drift gas inlet 116 arranged towards the middle of the drift chamber 104, a first drift gas outlet 118 arranged between the drift gas inlet 116 and the first ion source 102-1, 108-1, and a second drift gas outlet 118 arranged between the drift gas inlet 116 and the second ion source 102-2, 108-2. Accordingly, the IMS may be configured to provide a flow of drift gas in a direction generally opposite both negative and positive ion's path of travel from their source to the first or second detector 118. Example drift gases include, but are not limited to, nitrogen, helium, air, air that is re-circulated (e.g., air that is cleaned and/or dried), the drift gas may be doped for example with ammonia or acetone, or another material.

In operation, a flow of gaseous fluid may be drawn past the inlets 102 of each of the first ion source 102-1, 108-1 and the second ion source 102-2, 108-2. The controller 112 may trigger the ion sources to obtain a sample of gaseous fluid from this flow to be ionised. The controller 112 may operate the first ion source 102-1, 108-1 to ionise the sample to provide positive ions. The controller 112 can also operate the second ion source 102-2, 108-2 to provide negative ions.

The controller 112 may then operate an ion gate to allow positive ions to travel from the first ion source 102-1, 108-1 along the drift chamber 104, down the voltage profile provided by the electric field applier, and through the flow of drift gas to the collection electrode of the first detector 106-1. The controller 112 may also operate another ion gate to allow negative ions to travel in the other direction, from the second ion source 102-2, 108-2 up the voltage profile provided by the electric field applier, and through the flow of drift gas to the collection electrode of the second detector.

The controller 112 may be configured to stagger the timing of opening of the ion gates so that the positive ions and negative ions need not travel along the drift chamber 104 at the same time. For example, the controller 112 may be configured to select the timing of opening the first ion gate based on the timing of opening the second ion gate.

The controller 112 may also be configured to select the timing of operation of the each detector based on the timing of operation of the adjacent ioniser. For example, the controller 112 may select timing of operation of the second detector based on the timing of operation of the first ioniser, for example the controller 112 may be configured so that when the first ioniser is applying energy to ionise a sample, the second detector is switched off, for example the collecting electrode may be isolated from the signal determiner. In the same way, the timing of operation of the first detector may be selected based on the timing of operation of the second ioniser to avoid detector and ioniser being operated together.

The collection electrode of each of the first detector and the second detector may also be configured to provide an ion gate. For example, the ion gate 106 of the first ion source 102-1, 108-1 may provide the collection electrode of the second detector. Accordingly, the signal determiner of the second detector may be coupled to detect the arrival of negative ions at the first ion gate 106 (second collection electrode) from the second ion source 102-2, 108-2 and vice versa. For example, the first ion gate 106 may be operable in a gating mode to control the passage of positive ions from the first ion source 102-1, 108-1 to the first detector, and in an ion detection mode for collecting negative ions to be detected by the second detector. One example of a combined ion gate 106 and detector suitable for use in this way is described below with reference to FIG. 2.

In some other examples, the collection electrode of each detector may be provided by a repeller electrode used to move ions away from the ion source which generated the ions. For example, the first ion source 102-1, 108-1 may comprise a first repeller coupled to the voltage provider 114 for moving positive ions towards the first detector. This first repeller electrode may however also be coupled to the signal determiner of the second detector so that the repeller electrode can act as a collection electrode for detecting the arrival of negative ions but also to repel positive ions. Where a repeller electrode is used in this way a screening electrode may be arranged to inhibit ions from inducing a signal in the detector prior to arrival of the ions at the repeller electrode. One example of a combined repeller electrode and detector is described with reference to FIG. 3. It will however be appreciated that other structures in the IMS may be used for detecting ions.

FIG. 2 includes FIG. 2-A and FIG. 2-B. FIG. 2-A shows an illustration of a combined ion gate and detector. FIG. 2-B illustrates a plan view of a part section of an IMS apparatus 100' comprising the combined ion gate and detector illustrated in FIG. 2-A.

FIG. 2-A shows an ion gate 106 arranged to provide an ion detector for an ion mobility spectrometer. The ion gate 106 shown in FIG. 2-A comprises a plurality of conductors arranged to provide a Bradbury-Nielsen gate. Tyndall-Powell ion gate arrangements, and other arrangements, may also be used.

The ion gate 106 comprises two electrodes each comprising a plurality of elongate conductors which may be aligned with each other, for example in parallel, to provide a grid of conductors. Alternate ones of the conductors may be electrically coupled together to provide independently controllable electrodes. As illustrated in FIG. 2-A (and shown in section view in FIG. 2-B) the conductors of the first electrode of the ion gate 106 may be interleaved between the conductors of the first electrode. In some examples the first and second electrodes may be co-planar e.g. the conductors may be interdigitated. In some examples however the two electrodes may be offset from each other, for example offset in the direction of travel of ions along the IMS cell.

A gate controlling voltage provider 114 is coupled to the ion gate 106 for controlling the voltage of the first electrode and the second electrode. The first electrode may be coupled to a first output of the voltage provider 114. The second ion gate 106 electrode may be coupled to a second output of the voltage provider 114.

A signal determiner 110 is coupled to one of the first and second electrodes for detecting the arrival of ions at that electrode. The signal determiner 110 may be coupled to provide a detection signal to a controller of an IMS apparatus (such as the controller 112 of the IMS 100 shown in FIG. 1), for example to be used in identifying material from a sample, for example by providing a plasmagram.

The signal determiner 110 may comprise an isolation amplifier, for example a differential amplifier adapted for measurement of small signals in the presence of a high common mode voltage (e.g. potential differences between instrument ground and signal ground). The signal determiner may be configured to provide a resolution in the range of picoamps, and may be configured to provide this in the presence of common mode voltages of at least 100 Volts, for example at least 500 Volts. In some embodiments the common mode voltage may be associated with the voltage applied between the gate electrodes to close the gate, and may for example be about 100 Volts. In some configurations the gate as a whole may be at an average voltage of at least 500 Volts and the isolation amplifier may be configured to provide picoamp resolution in these circumstances. These are just examples and some implementations may require greater or lesser resolution and may be used in the presence of greater or lesser common mode voltages. One example of a suitable isolation amplifier is the ISO124 produced by Texas Instruments Inc. or the IFS series of amplifiers produced by XP Power, Horseshoe Park, Pangbourne, Reading, Berkshire, UK, RG8 7JW. Other types of isolation amplifiers may be used.

The voltage provider 114 is configured to control the gate 106 by controlling the relative voltage of the first electrode and the second electrode. This can control the passage of ions through the ion gate 106. For example, the voltage provider 114 may be configured to hold the voltage of one electrode fixed (e.g. coupled to a reference voltage) and to vary the voltage of the other electrode to open and close the gate. For example, the gate may be "open" when the potential on the first and second electrodes is similar, for example when the electrodes are at an equal potential. The voltage provider 114 may be configured to deflect ions travelling through the gate by applying a voltage between the first electrode and the second electrode. It will be appreciated that "closing" the gate 106 in this way may deflect the path of travel of an ion through the gate, for example an ion may be drawn towards, for example forced onto, one electrode or the other.

In examples where a first electrode of the ion gate 106 is held at a selected (e.g. fixed) voltage, and the signal determiner may be coupled to detect the arrival of ions at the first electrode, for example an input of the signal determiner may be coupled to the fixed electrode. For example the detector may comprise an isolation amplifier having an input coupled to the fixed electrode, the other input of the amplifier may be coupled to its output, for example via a capacitance of some kind, for example the amplifier may be configured as an integrator. In some embodiments the controller may be configured to protect the signal determiner from transient signals associated with opening and closing the ion gate, for example the controller may be configured to isolate an input of the signal determiner (e.g. an amplifier input) from the ion gate before opening or closing the gate, and to reconnect the input to the ion gate a selected time after the gate has been closed. An electrically operable switch for example a transistor or relay, or other means of isolating the input of the amplifier may be provided and coupled to the controller and an input of the signal determiner for this purpose.

FIG. 2-B illustrates a view of a dual-mode IMS cell comprising a drift chamber 104, a first ion source 102-1, 108-1 and a first ion detector which comprises an ion gate 106-1 arranged to provide an electrode of a detector, for example the ion gate 106-1 of FIG. 2-B may comprise an apparatus such as that described with reference to FIG. 2-A.

The IMS cell illustrated in FIG. 2-B also comprises a second ion source 102-2, 108-2 and a second ion detector 106-2 which may also be provided by an ion gate. The first ion source 102-1, 108-1 and the second detector 106-2 are arranged at one end of the drift chamber 104 and the second ion source 102-2, 108-2 and the first detector 106-1 are arranged at the other end of the drift chamber 104.

The apparatus illustrated in FIG. 2-B comprises an inlet 102-2 for introducing material to be ionised, and an ioniser 108-2 arranged for ionising the material. Together the inlet 102-2 and ioniser 108-2 can provide the second ion source 102-2, 108-2, for example such as the ion source described above with reference to FIG. 1. Other kinds of ion source may also be used.

As illustrated in FIG. 2-B, the IMS 100' comprises an inlet 102-1, 102-2 at each end, one for the first ion source 102-1, 108-1 and one for the second ion source 102-2, 108-2. It can be seen from FIG. 2-B that these inlets may not be aligned with each other and may for example be offset from the central axis of the drift chamber 104. This may also be the case in other embodiments such as those described with reference to FIG. 1 and FIG. 3-B and other embodiments.

The ion gate 106-1 (which may provide the collecting electrode of the first detector) is arranged across the IMS cell to enclose the second ion source 102-2, 108-2 and may be coupled to a voltage provider 114 and ion gate 106 as illustrated in FIG. 2-A. In the example illustrated in FIG. 2-B, the IMS cell also includes a screening electrode 122 and drift electrodes 120 spaced apart from each other and the ion gate 106 along the IMS cell. The screening electrode 122 may be arranged in the IMS cell between the drift electrodes 120 and the gate 106-1. The drift electrodes 120, the screening electrode 122, and the ion gate 106 may be coupled to the voltage provider 114.

The drift electrodes 120 may be configured to provide a voltage profile along the drift chamber 104 to move positive ions in one direction and to move negative ions in the other direction. The screening electrode 122 may be configured to at least partially shield the adjacent detector from electric fields so as to inhibit the detection of ions travelling from the second ion source 102-2, 108-2 prior to their arrival at the ion gate 106-1 of the first detector.

Operation of the IMS cell shown in FIG. 2-B may proceed as described above with reference to FIG. 1. The voltage provider 114 may open the ion gate 106-1 to allow ions to travel from the second ion source 102-2, 108-2 along the drift chamber 104 towards the second detector 016-2. The voltage provider 114 then closes the ion gate 106-1, by applying a voltage difference between the first electrode and the second electrode of that gate. With that gate 106-1 closed it can operate to detect ions, for example the voltage applied to close the gate may be selected to cause positive ions to be collected on the gate electrode to which the detector is coupled. A signal determiner may be configured to detect the arrival of ions during time intervals in which the ion gate 106-1 is closed and to switch off or decouple from the ion gate 106-1 during time intervals when the ion gate 106-1 is open.

FIG. 3 shows an alternative arrangement of an ion source in an IMS apparatus 100" suitable for use in a dual mode cell. The ion source illustrated in FIG. 3 comprises an inlet 102 for introducing material to be ionised, and an ioniser arranged for ionising the material. The apparatus illustrated in FIG. 3 comprises a repeller electrode 119. The repeller electrode 119 may be coupled to a voltage provider 114 and used with the drift electrodes 120 to provide a voltage profile for moving ions away from the ioniser along the drift chamber 104 towards a detector (and another ion source) at the other end of the drift chamber 104 (not shown in FIG. 3). The apparatus of FIG. 3 may comprise an ion gate such as a Bradbury-Neilsen or Tyndall Powell gate.

The repeller electrode 119 may also be coupled to a signal determiner 110 adapted to provide a detection signal in response to the arrival of ions at the repeller electrode 119. For example, the voltage provider 114 may be configured to move positive ions away from the repeller electrode 119 and the signal determiner may be configured to detect the arrival of negative ions at the repeller electrode 119 (or vice versa).

The signal determiner 110 illustrated in FIG. 3 may comprise an isolation amplifier, for example a differential amplifier adapted for measurement of small signals in the presence of a high common mode voltage (e.g. potential differences between instrument ground and signal ground). As explained above with reference to the embodiments illustrated in FIG. 1, the signal determiner may be configured to provide resolution of currents in the picoamp range in the presence of common mode voltages associated with the voltage at the repeller electrode, for example a voltage of at least 100 Volts, for example at least 600 Volts.

The apparatus illustrated in FIG. 3 may comprise a controller (not shown in FIG. 3) configured to control the timing of operation of the ioniser 108'. This controller may be configured to select the timing of operation of the signal determiner 110 based on the timing of operation of the ioniser 108. For example this controller may be configured to operate the signal determiner to detect the arrival of ions during intervals when the ioniser 108 is switched off. The controller may be configured to protect the signal determiner from transient signals associated with operating the ioniser, for example the controller may be configured to isolate an input of the signal determiner (e.g. an amplifier input) from the repeller electrode before operating the ioniser, and to reconnect the input a selected time after the ioniser has stopped operating. An electrically operable switch for example a transistor or relay, or other means of isolating the input of the amplifier may be provided and coupled to the controller and an input of the signal determiner for this purpose.

As illustrated, the apparatus in FIG. 3 may also comprise a screening electrode 122 arranged to inhibit ions from being detected by the detector prior to their arrival at the electrode. For example, the screening electrode may comprise a grid, for example a mesh, for example a honeycomb grid, and may be arranged to at least partially screen the repeller electrode 119 from electric fields provided by ions travelling from the drift chamber 104 towards the repeller electrode 119.

In operation, a sample of material to be ionised may be drawn in through the inlet 102, and the controller 112 may operate the ioniser to ionise the sample of material. The controller 112 may then open the ion gate 106' to allow ions from the sample to travel along the drift chamber 104 towards a detector at the other end of the drift chamber 104. The ioniser may then be switched off, and ions produced by an ion source at the other end of the drift chamber 104 may then be allowed to travel along the drift chamber 104 towards the repeller electrode 119. During the interval when the ioniser is switched off, the controller 112 may operate the signal determiner to detect the arrival of ions at the repeller electrode 119 to obtain a detection signal indicating the time of flight of the ions along the drift chamber 104. The screening electrode may inhibit electric fields from these ions from inducing a signal from the repeller electrode to the signal determiner prior to their arrival at the repeller electrode 119, or at least until they have passed the screening electrode 122.

It will be appreciated that in some embodiments either the ion gate, or the repeller electrode 119 or both may be used to detect ions and in some embodiments other structures within the IMS may be used to detect ions. For example, in some embodiments electrodes are placed in the path of ions along the drift chamber 104 and may be used to detect ions. These electrodes may be used solely for the purposes of detecting ions or may also serve other purposes—for example some embodiments of IMS devices comprise ion modifier electrodes adapted to apply RF electric fields to ions, for example to fragment the ions. In some embodiments these and other structures may be coupled to signal determiners to provide a detector.

Other examples and variations will be apparent to the skilled addressee in the context of the present disclosure. For example, embodiments of the disclosure relate to time or flight IMS and other kinds of IMS. Some embodiments use a non-continuous ionization source such as a corona discharge source. Some embodiments use a continuous ionization source such as Ni-63 or Am-241.

Embodiments of the disclosure comprise a TOF-IMS cell having series of electrically separate field defining electrodes and which has an ion gate located at both ends. Behind each ion gate there may be an ion source and further field defining electrodes to form two separate ionization regions. These ionization regions may generate positive and negative charged ions respectively. At the far end of each ionization region there may be a further field defining electrode arrangement which could be a single flat plate or grill, a flat plate or grill with a hole to allow passage of sample or a flat plate or grill with a further electrically separate grill which could be held at a discrete voltage with respect to the other grill or plate. This plate or grill may be configured to repel ions towards the ion gate separating the source region with the drift region of the proposed IMS cell.

In order to avoid injection of neutral gas molecules into the drift region of the IMS cell in some embodiments a drift gas is flowed into a point or points approximately in the center of the length of the drift region. It may be desirable to introduce this drift gas evenly around the circumference of the drift region for example through a plurality of vents distributed about the circumference of the drift chamber. The drift gas may be extracted from the IMS cell at a point within each ionization source region either before or after the ionization source in terms of drift gas flow direction.

Sample material may be introduced into the IMS cell using one or more of a pinhole/capillary interface, a multi-pinhole/capillary interface or a membrane interface may also be used (e.g. a "pepperpot" configuration). In the case of a membrane based interface then it may be useful to provide an additional pneumatic system to pull sample from the internal face of the membrane and carry it into the ioniser.

In some embodiments one or more ion modification grids may be provided inside the drift region so that ion modification (for example fragmentation using RF energy) can be carried out on molecular ion clusters to gain further spectral information.

One possible way of operating the invention, assuming a pinhole sampling inlet, would be to draw sample into the ionization regions where it would be ionized. Ions could then be gated into the drift region of the device and drawn along the drift region under the force of the electric field. Ions would contact a grid structure (e.g. at the opposite end of the IMS cell to that at which they were generated to give an ion current to produce both positive and negative ion spectra. An alternative arrangement would set the grid to be open after the initial ion pulse from the source had decayed and allow the ions generated to contact the repeller electrode at the end opposite end of the IMS cell to which they were generated, again generating ion current and producing an IMS spectrum.

The above operating regime assumes that there will be no interaction between the differently charged ion species as they pass each other on their journeys through the drift region. If such interaction were a concern then the ion gates could be operated in an alternate fashion (e.g. staggered opening times) to collect spectra from one ion charge then the second ion charge.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

The voltage providers described herein may comprise an electrical power supply and one or more transformer stages, inverters, and/or rectifiers for applying alternating or direct current. The voltage provider may be coupled to an external or internal power source such as a battery, or a fuel cell, or an external supply of alternating or direct current.

The activities and apparatus outlined herein may be implemented using controllers and/or processors which may be provided by fixed logic such as assemblies of logic gates or programmable logic such as software and/or computer program instructions executed by a processor. Other kinds of programmable logic include programmable processors, programmable digital logic (e.g., a field programmable gate array (FPGA), an erasable programmable read only memory (EPROM), an electrically erasable programmable read only memory (EEPROM)), an application specific integrated circuit, ASIC, or any other kind of digital logic, software, code, electronic instructions, flash memory, optical disks, CD-ROMs, DVD ROMs, magnetic or optical cards, other types of machine-readable mediums suitable for storing electronic instructions, or any suitable combination thereof.

The invention claimed is:

1. An ion mobility spectrometer comprising:
   a first ion source for providing positive ions to be analysed;
   an electric field applier arranged to provide an electric field configured to move the positive ions in a first direction towards a first ion detector adapted for detecting the positive ions; and
   a second ion source for providing negative ions to be analysed, wherein the electric field applier is arranged to move the negative ions in a second direction different from the first direction, towards the first ion source and towards a second ion detector adapted for detecting the negative ions.

2. The ion mobility spectrometer of claim 1, wherein the first ion source comprises a first ioniser configured to provide ions by applying ionising energy to a gaseous fluid, and the ion mobility spectrometer comprises a controller configured to select the timing of operation of the second ion detector based on the timing of operation of the first ioniser.

3. The ion mobility spectrometer of claim 1, further comprising a first ion gate arranged to control the passage of ions from the first ion source towards the first ion detector, and a second ion gate arranged to control the flow of ions from the second ion source towards the second ion detector.

4. The ion mobility spectrometer of claim 3, wherein the second ion detector is coupled to the first ion gate to detect ions arriving at the first ion gate.

5. The ion mobility spectrometer of claim 4, wherein the first ion gate is operable in a gating mode to control the passage of ions from the first ion source to the first ion detector, and in an ion detection mode for collecting ions to be detected.

6. The ion mobility spectrometer of claim 1, in which the first ion source comprises a first repeller operable to move positive ions towards the first detector, and further operable to detect the arrival of negative ions.

7. The ion mobility spectrometer of claim 1, wherein the first ion source and the second ion source are separated from each other by a drift region.

8. The ion mobility spectrometer of claim 7, wherein the electric field applier is arranged to provide a voltage profile that is symmetric about a mid-point of the drift chamber.

9. The ion mobility spectrometer of claim 7, further comprising a drift gas inlet in the drift region arranged to provide a flow of drift gas towards the first ion source and towards the second ion source.

10. The ion mobility spectrometer of claim 9, further comprising a first drift gas outlet arranged so that drift gas flows from the drift gas inlet to the first ion source and out of the first drift gas outlet.

11. The ion mobility spectrometer of claim 9, further comprising a second drift gas outlet arranged so that drift gas flows from the drift gas inlet to the second ion source and out of the second drift gas outlet.

12. The ion mobility spectrometer of claim 1, further comprising a flow passage arranged to provide a flow of gaseous fluid past a first inlet arranged to provide a sample to be ionised from the flow to the first ion source and past a second inlet arranged to provide a sample to be ionised from the flow to the second ion source.

13. The ion mobility spectrometer of claim 1, further comprising a controller configured to control the release of ions from at least one of the first ion source or the second ion source based on the timing of a release of ions from the respective other one of the at least one of the first ion source or the second ion source.

14. The ion mobility spectrometer of claim 13, wherein controlling the release of ions comprises controlling operation of an ion gate.

15. A method of operating an ion gate for an ion mobility spectrometer, the method comprising:
    opening the ion gate to allow first ions to pass through the ion gate;
    closing the ion gate to inhibit the passage of ions through the ion gate; and
    detecting arrival of second ions at the ion gate while the gate is closed, wherein the second ions have charge of a different sign to the first ions.

16. The method of claim 15, wherein detecting comprises collecting ions on an electrode of the ion gate.

17. The method of claim 15, wherein the ion gate comprises two electrodes.

18. The method of claim 17, further comprising applying a voltage between the two electrodes to collect positive ions on one of the two electrodes and negative ions on the other one of the two electrodes, and wherein detecting the arrival of second ions at the ion gate comprises detecting the arrival of the positive or negative ions at the corresponding one of the two electrodes.

19. A method of operating a pair of ion gates of an ion mobility spectrometer, the method comprising:
    opening a first one of the pair of ion gates to allow ions to pass towards a second one of the pair of ion gates, wherein the first one of the pair of ion gates and the second one of the pair of ion gates are separated from each other by a drift chamber; and
    detecting arrival of the ions at the second one of the pair of ion gates.

20. The method of claim 19, comprising holding the second ion gate closed to detect arrival of the ions.

* * * * *